Figure 1:
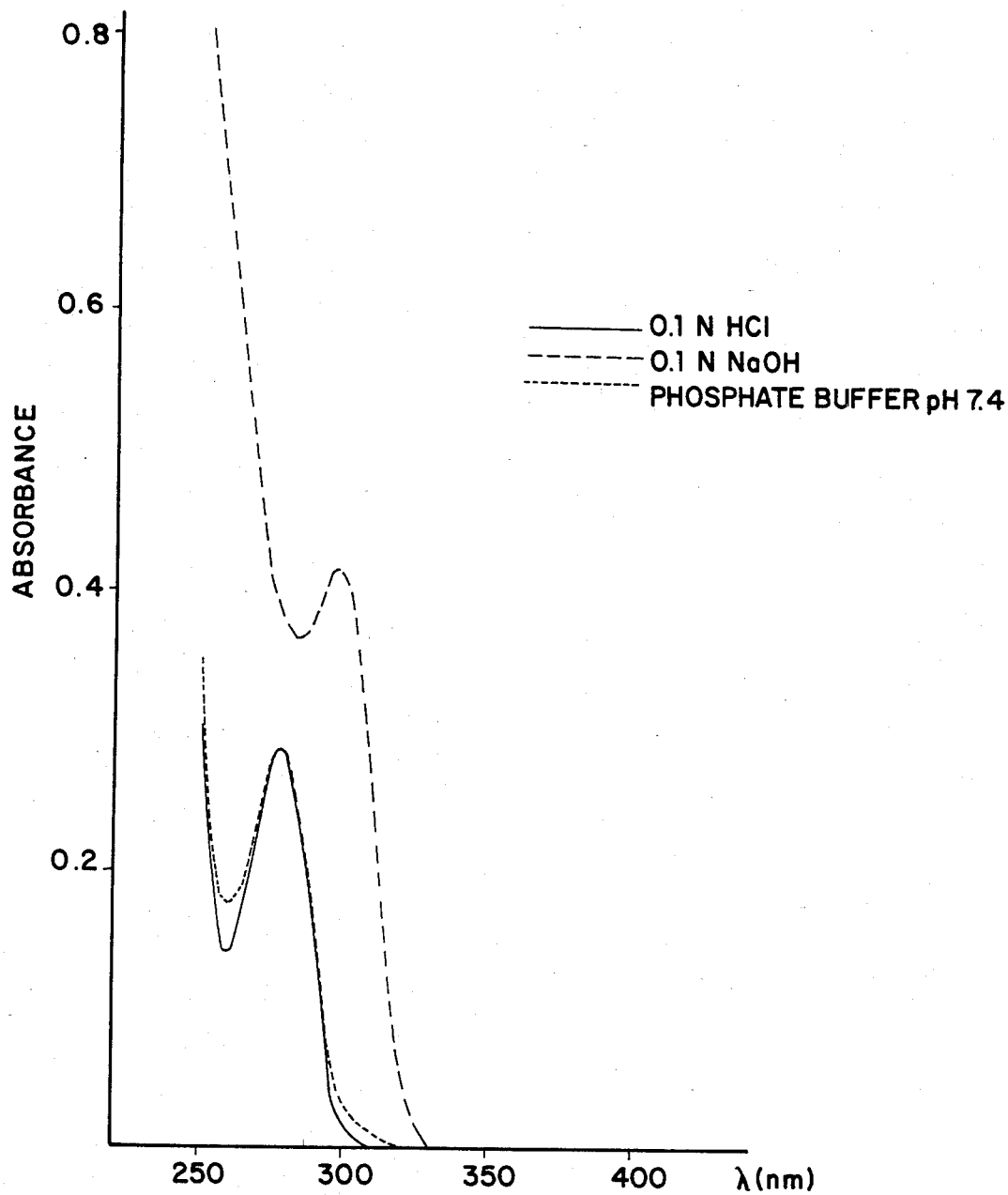

United States Patent [19]

Borghi et al.

[11] Patent Number: 4,542,018

[45] Date of Patent: Sep. 17, 1985

[54] TEICHOMYCIN $A_2$ PURE SINGLE FACTORS 1, 2, 3, 4 AND 5 AND METHOD FOR THEIR PRODUCTION

[75] Inventors: Angelo Borghi; Rosa Pallanza; Carolina Coronelli, all of Milan; Giovanni Cassani, Pavia, all of Italy

[73] Assignee: Gruppo Lepetit S.p.A., Milan, Italy

[21] Appl. No.: 502,043

[22] Filed: Jun. 7, 1983

[30] Foreign Application Priority Data

Jun. 8, 1982 [GB] United Kingdom ............... 8216590

[51] Int. Cl.$^4$ ............................................. A61K 35/74
[52] U.S. Cl. ................................... 424/119; 424/124
[58] Field of Search ......................................... 424/119

[56] References Cited

U.S. PATENT DOCUMENTS 4,239,751 12/1980 Coronelli et al. ................... 424/120

Primary Examiner—Jerome D. Goldberg
Attorney, Agent, or Firm—William J. Stein; Gary D. Street; Stephen L. Nesbitt

[57] ABSTRACT

The invention refers to an individual antibiotic substance selected from the group consisting of Teichomycin $A_2$ factor 1, Teichomycin $A_2$ factor 2, Teichomycin $A_2$ factor 3, Teichomycin $A_2$ factor 4 and Teichomycin $A_2$ factor 5 in substantially pure form, and to the method of producing them by recovery from Teichomycin $A_2$, a known antibiotic substance, by means of high-efficiency chromatographic methods. The single pure Teichomycin $A_2$ factor 1, Teichomycin $A_2$ factor 2, Teichomycin $A_2$ factor 3, Teichomycin $A_2$ factor 4 and Teichomycin $A_2$ factor 5 are biologically distinguishable from Teichomycin $A_2$ in that they have a higher degree of antibiotic activity against susceptible microorganisms.

4 Claims, 13 Drawing Figures

U.V. ABSORPTION SPECTRUM OF TEICHOMYCIN $A_2$ FACTOR 1

INFRARED SPECTRUM (NUJOL) OF TEICHOMYCIN $A_2$ FACTOR 1

U.V. ABSORPTION SPECTRUM OF TEICHOMYCIN $A_2$ FACTOR 2

INFRARED SPECTRUM (NUJOL) OF TEICHOMYCIN $A_2$ FACTOR 2

U.V. ABSORPTION SPECTRUM OF TEICHOMYCIN A2 FACTOR 3

U.V. ABSORPTION SPECTRUM OF TEICHOMYCIN A$_2$ FACTOR 4

INFRARED SPECTRUM (NUJOL) OF TEICHOMYCIN A₂ FACTOR 4

U.V. ABSORPTION SPECTRUM OF TEICHOMYCIN A₂ FACTOR 5

INFRARED SPECTRUM (NUJOL) OF TEICHOMYCIN $A_2$ FACTOR 5

TEICHOMYCIN $A_2$ PURE SINGLE FACTORS 1, 2, 3, 4 AND 5 AND METHOD FOR THEIR PRODUCTION

The present invention refers to an individual antibiotic substance selected from the group consisting of Teichomycin $A_2$ factor 1, Teichomycin $A_2$ factor 2, Teichomycin $A_2$ factor 3, Teichomycin $A_2$ factor 4 and Teichomycin $A_2$ factor 5 in substantially pure form, and to the method of producing it.

Teichomycin $A_2$ is one of the several different antibiotic substances obtained by cultivating the strain *Actinoplanes teichomyceticus* nov.sp. ATCC 31121 in a culture medium containing assimilable sources of carbon, nitrogen and inorganic salts (see Belgian Pat. No. 839,259). According to the procedure described in the above cited patent an antibiotic mixture containing Teichomycin $A_1$, $A_2$, and $A_3$ is recovered from the separated fermentation broth by extraction with a suitable organic solvent immiscible with water and precipitation from the extracting solvent according to common procedures. Teichomycin $A_2$ is then separated from the antibiotic mixture thus obtained by means of column chromatography on Sephadex ®. Teichomycin $A_2$, after being further purified by passing through a sulfonated polystyrene resin, is then characterized by a wide series of different chemico-physical parameters including the $R_f$ values in a set of paper and thin layer chromatographic systems where this compound behaved as a true unitary product.

It has now been found unexpectedly that Teichomycin $A_2$ actually comprises a mixture of several co-produced closely related antibiotic materials, the main factors of which have been named Teichomycin $A_2$ factor 1, Teichomycin $A_2$ factor 2, Teichomycin $A_2$ factor 3, Teichomycin $A_2$ factor 4 and Teichomycin $A_2$ factor 5. It has also been found that these pure single factors are biologically distinguishable from Teichomycin $A_2$ complex in that they have a higher degree of antibiotic activity against susceptible microorganisms.

The antibiotic substances of the present invention are prepared starting from Teichomycin $A_2$ which is described in the Belgian patent cited above, by separating the antibiotic complex into the single factors by means of high-efficiency chromatographic methods and recovering the main ones.

The terms "Teichomycin $A_2$", "Teichomycin $A_2$ complex" or "antibiotic complex" as used in this specification refer to the mixture containing the above five co-produced antibiotic factors obtainable for example by the teaching of Belgian Pat. No. 839,259, which is incorporated herein by reference, and there named Teichomycin $A_2$.

Separation of the complex into the main pure single factors may be achieved by reversed-phase partition or ion-exchange chromatography. In the former case inactivated silica gel is conveniently used as the column packing and a gradient elution of acetonitrile/aqueous ammonium formate as the developer, while in the latter case a weak gel-type anion exchanger is suitably employed as the stationary phase and aqueous buffers or mixtures of aqueous buffers and non-aqueous solvents as the eluting systems. In particular, optimum separating results have been obtained by passing a solution of Teichomycin $A_2$ dissolved in a mixture of diluted aqueous ammonium formate and acetonitrile through a silanized silica gel column and developing the column with a gradient elution in the same solvent system. Good results are obtained also by using the diethylaminoethyl derivative of agarose as the stationary phase and carrying out the separation by progressive elution with buffer solutions or mixtures of buffer solutions and non-aqueous water-miscible solvents.

The separation procedure is monitored by HPLC. Fractions with similar HPLC profile are combined, if desired, further purified by preparative HPLC, and desalted. From these solution the single factors are then recovered by evaporating the organic solvents, stripping off water to a small volume and adding an excess of an organic solvent in which the compounds are not soluble to precipitate the obtained products.

The following specific example is provided for to better illustrate the process of the present invention. Said example however should not be construed to limit the invention to the particular conditions there disclosed.

SEPARATION OF TEICHOMYCIN $A_2$ FACTORS 1, 2, 3, 4 AND 5

Ten grams of Teichomycin $A_2$ complex obtained by the process described in Belgian Pat. No. 839,259 are dissolved in 1 liter of a 0.2 % ammonium formate-acetonitrile (9:1) mixture and adjusted at pH 7.5 with 1 N NaOH. This solution is passed through a column containing 500 grams of silanised silica gel 60 (Merck). The column isthen eluted with a linear gradient from 10% to 20% acetonitrile in a 0.2% ammonium formate solution in a total volume of 10 liters.

Fractions of ~20 ml are collected and checked by means of HPLC.

In following Table I the retention times ($t_R$) for Teichomycin $A_2$ factors 1, 2, 3, 4 and 5 in a representative HPLC separation are reported (the operative conditions are indicated below the Table):

TABLE I

| Teichomycin $A_2$ factor | Retention time (minutes) |
| --- | --- |
| 1 | 21.2 |
| 2 | 22.6 |
| 3 | 23.3 |
| 4 | 25.8 |
| 5 | 26.4 |
| 3,5-dihydroxytoluene (internal standard) | 8.84 |

Column: 5μ Zorbax ® ODS (Du Pont)
Mobile Phase: Linear gradient from 0%B to 50%B in A in 40 minutes
(A) 25 mM $NaH_2PO_4$/Acetonitrile (9:1) buffered at pH 6.0 with 0.1N NaOH
(B) 25 mM $NaH_2PO_4$/Acetonitrile (3:7) buffered at pH 6.0 with 0.1N NaOH
Flow: 2 ml/min.
Detector: U.V. Photometer at 254 nm.

Fractions with similar HPLC profile are combined and the organic solvent is evaporated under reduced pressure. The aqueous solutions left, are passed through a column containing 10 grams of silanized silica gel (60) (Merck). The column is washed with distilled water in order to eliminate the ammonium formate and then eluted with 50% aqueous acetonitrile.

The eluate is concentrated to a small volume by adding butanol to facilitate the evaporation of the water and then precipitated with a 1:1 acetone-ethyl ether mixture. Pure Teichomycin $A_2$ factor 1 (410 mg) and factor 2 (770 mg) are obtained by the above procedure. Teichomycin A$_2$ factor 3 as a 1:1 mixture with Teichomycin A$_2$ factor 2 is further purified by HPLC on a semipreparative column at the following operating conditions.

Column: Whatman Partisil ® ODS M 9 10/50
Mobile Phase: 0.2% ammonium formate in H$_2$O/acetonitrile (76:24).
Flow: 4.5 ml/min.
Detector: U.V. Photometer at 254 nm,
Load: 20 mg Also in this case purification is monitored by checking each fractions by HPLC.

Fractions containing pure Teichomycin A$_2$ factor 2 as well as fractions containing pure Teichomycin A$_2$ factor 3 are combined, desalted and precipitated as previously described. (Yield: 510 mg of Teichomycin A$_2$ factor 2 and 520 mg of Teichomycin A$_2$ factor 3).

Fractions containing factors 4 and 5 in 1:1 proportion (about 500 mg) obtained from the first column, are combined with another pool of fractions containing a mixture of factors 4 and 5 (about 490 mg) obtained in the same manner from a second parallel separation and are separated by semi-preparative HPLC using the same operating conditions seen above for the purification of Teichomycin A$_2$ factor 3, yielding 350 mg of Teichomycin A$_2$ factor 4 and 300 mg of Teichomycin A$_2$ factor 5.

CHEMICO-PHYSICAL CHARACTERISTICS OF THE PURE SINGLE FACTORS OF TEICHOMYCIN A$_2$

Teichomycin A$_2$ factor 1 is a white amorphous powder that upon heating, begins to darken at about 220° C. and is completely decomposed at 255° C., which has the following characteristics:

(a) It is freely soluble in water at pH>7.0 or at pH<2, in dimethylformamide, dimethylsulfoxide, and propyleneglycol; slightly soluble in methylcellosolve and glycerol; poorly soluble in methanol and ethanol, almost insoluble in chloroform, benzene, n-hexane, acetonitrile, ethyl ether, acetone, ethyl acetate, carbon tetrachloride (b) has an ultraviolet absorption spectrum, which is given in FIG. 1 of the accompanying drawings, that exhibits the following absorption maxima:

in 0.1N hydrochloric acid $$\lambda_{max} 278 \text{ nm } (E_{1\ cm}^{1\%} = 49.5)$$

in phosphate buffer pH 7.4:

$$\lambda_{max} 278 \text{ nm } (E_{1\ cm}^{1\%} = 50.0)$$

in 0.1N sodium hydroxide:

$$\lambda_{max} 297 \text{ nm } (E_{1\ cm}^{1\%} = 72.1)$$

Figure 2:
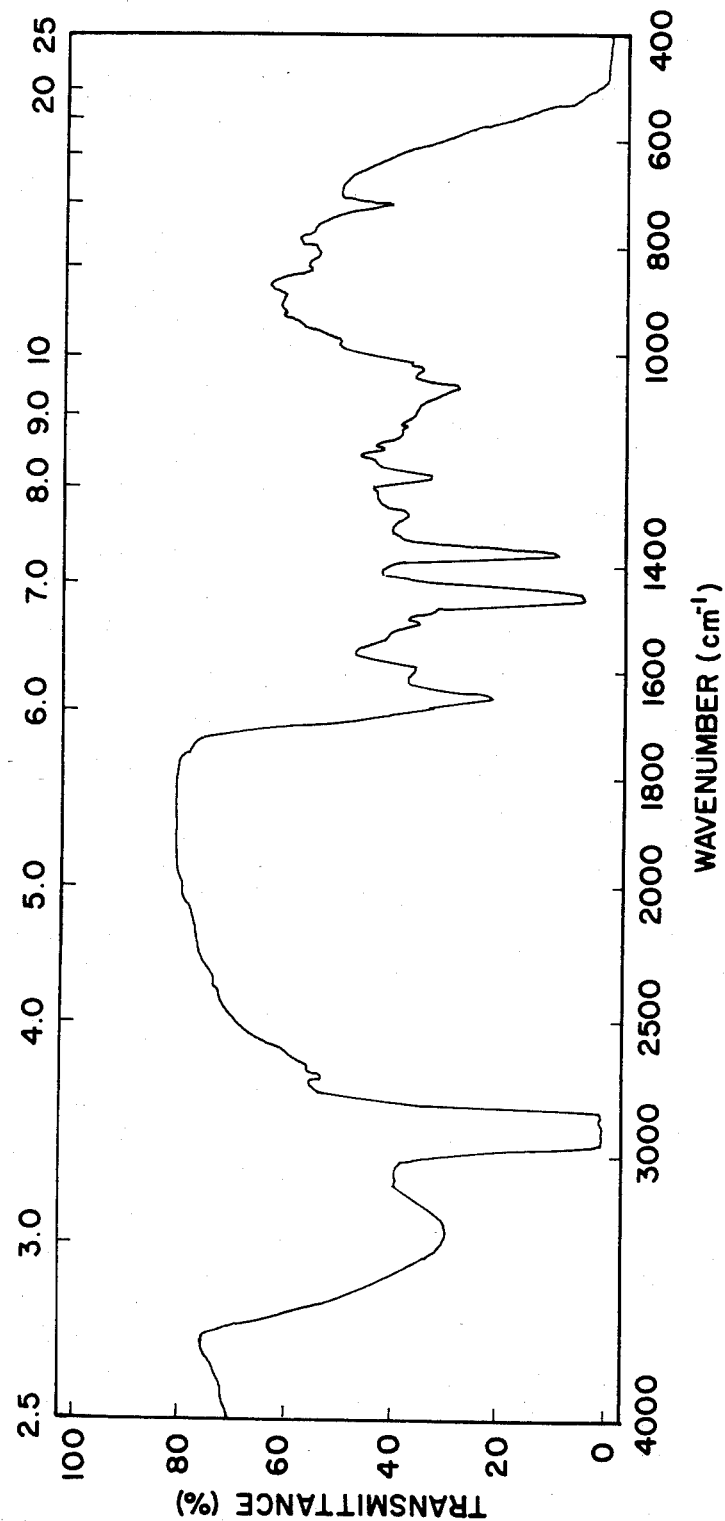

(c) an infrared absorption spectrum in nujol, shown in FIG. 2 of the accompanying drawings, with the following absorption maxima: 3700–3100, 2960–2840 (nujol), 1645, 1590, 1510, 1460 (nujol), 1375 (nujol), 1305, 1230, 1180, 1155, 1060, 1025, 970, 890, 845, 815, 720 (nujol);

(d) an elemental analysis, after the sample has been previously dried at about 140° C. under inert atmosphere (%Δw=8.5), which indicated the following approximate percentage composition (average): carbon 56.70%; hydrogen, 4.90%; nitrogen 6.65%; chlorine 3.80%; oxygen (by difference), 27.95%

(e) a retention time (t$_R$) of 21.2 minutes when analyzed by reversed phase HPLC using a 5μ Zorbax ® ODS column, and eluting with a linear gradient from 0% to 50% solution B in solution A in 40 minutes (solution A: 25 mM NaH$_2$PO$_4$/acetonitrile (9/1) buffered at pH 6.0 with 0.1N NaOH, solution B: 25 mM NaH$_2$PO$_4$/acetonitrile (3/7) buffered at pH 6.0 with 0.1N NaOH), with a flow rate of 2 ml/min.; (internal standard: 3,5-dihydroxy-toluene t$_R$ 8.84 minutes)

Figure 3:
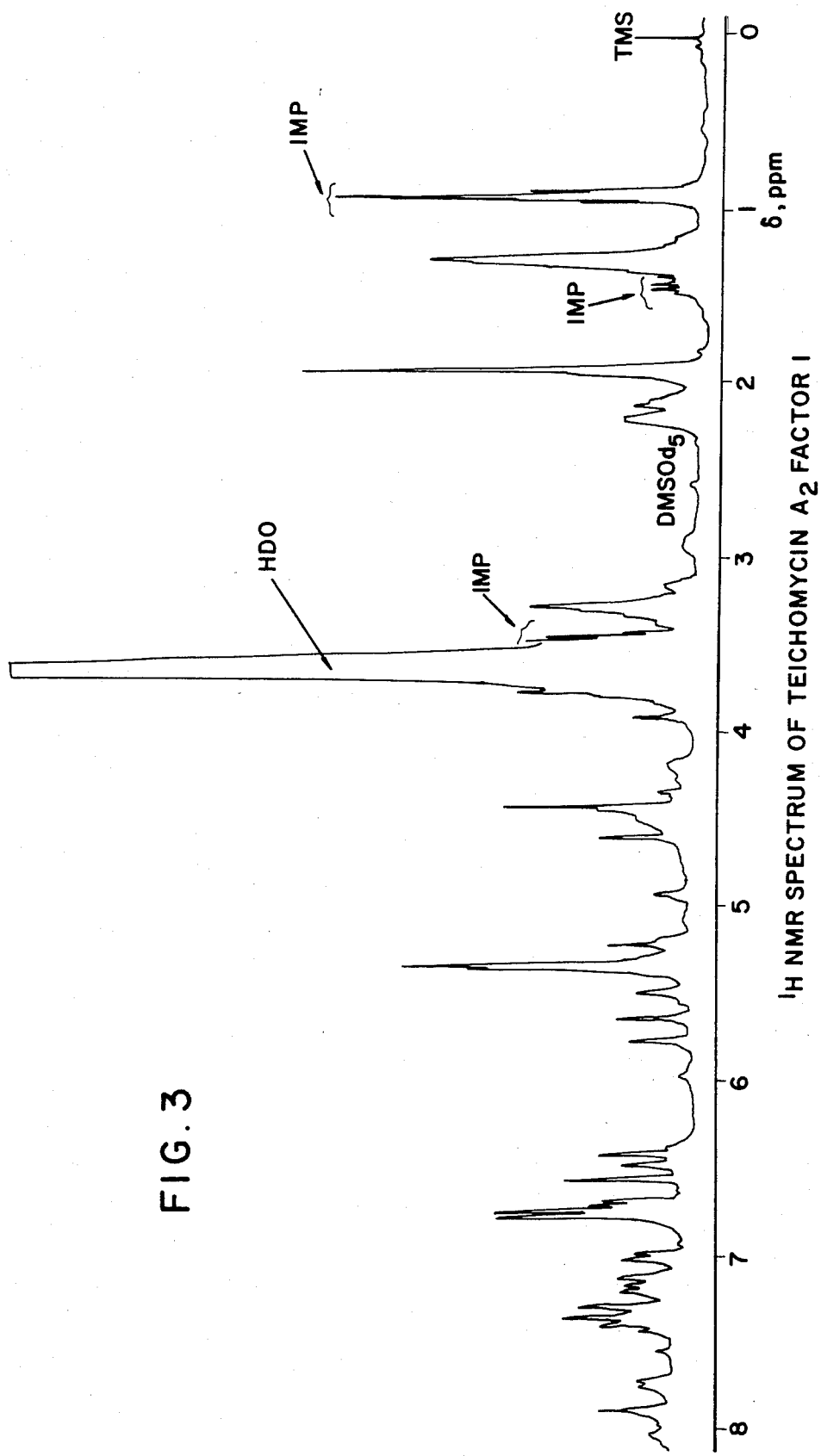

(f) the following groups of signals in the 270 MHz $^1$H NMR spectrum (the entire spectrum is shown in FIG. 3 of the accompanying drawings) registered in DMSO-d$_6$ with the addition of a few drops of D$_2$O (conc. 25 mg/0.5 ml) (TMS as internal standard: δ=0.00 ppm): 0.8–1.5(m); 1.7–2.3 (m); 2.7–4.0 (m); 4.0–4.7 (m) 4.8–5.8 (m); 6.2–8.1 (m)

(g) an acidic function capable of forming salts.
(h) a salifiable basic function
(g) a molecular weight of about 1875 as determined by mass spectrometric analysis using fast atom bombardment (FAB) as the ion source (for a presentation of FAB mass spectrometry, see for instance M. Barber et al. Nature, 293, No. 5830, 270–75 (1981)).

Figure 4:
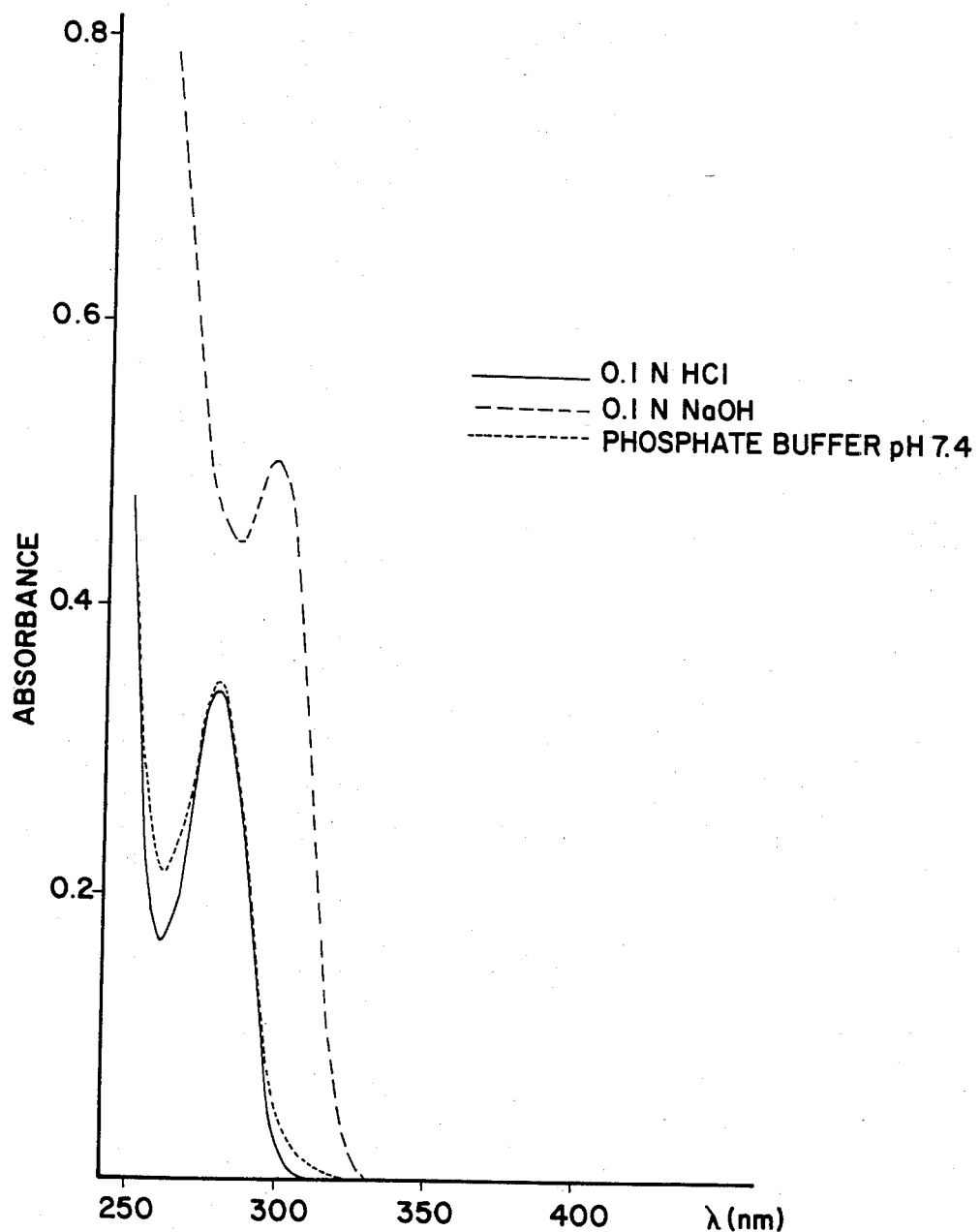

Teichomycin A$_2$ factor 2 is a white amorphous powder that commences to darken when heated to 210° C. and is completely decomposed at 250° C., which has the following characteristics:

(a) It is freely soluble in water at pH>7.0 or at pH<2 in dimethylformamide, dimethylsulfoxide and propyleneglycol; slightly soluble in methylcellosolve and glycerol; poorly soluble in methanol and ethanol; almost insoluble in chloroform, benzene, n-hexane, acetonitrile, ethyl ether, acetone, ethyl acetate, carbon tetrachloride (b) It has an ultraviolet absorption spectrum, which is given in FIG. 4 of the accompanying drawings, that exhibits the following absorption maxima:

in 0.1N hydrochloric acid:

$$\lambda_{max} 278 \text{ nm } (E_{1\ cm}^{1\%} = 48)$$

in phosphate buffer pH 7.4:

$$\lambda_{max} 278 \text{ nm } (E_{1\ cm}^{1\%} = 49.0)$$

in 0.1N sodium hydroxide:

$$\lambda_{max} 297 \text{ nm } (E_{1\ cm}^{1\%} = 70.0)$$

Figure 5:
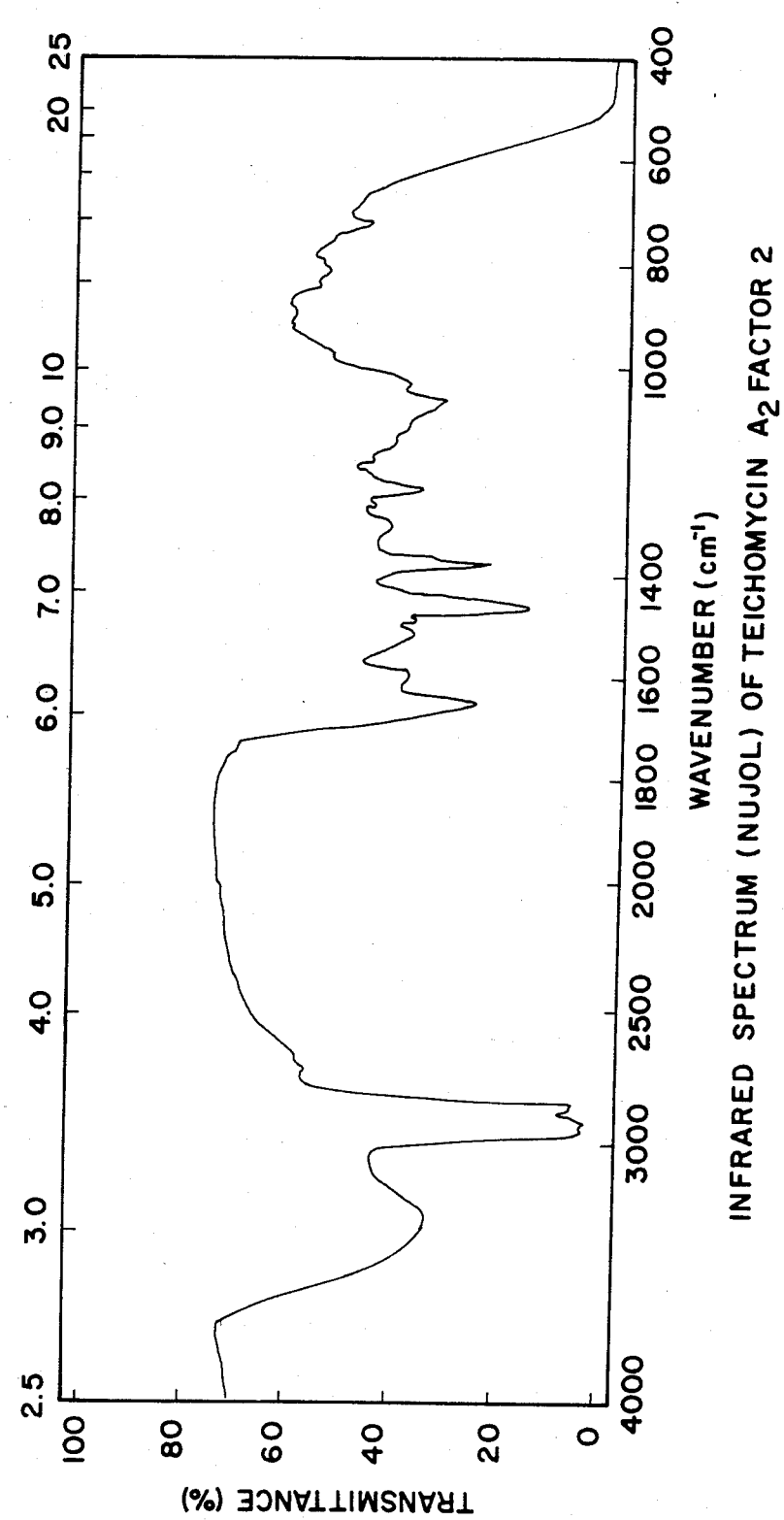

(c) an infrared absorption spectrum in nujol, shown in FIG. 5 of the accompanying drawings, with the following observable absorption maxima: 3700–3100, 2960–2860 (nujol), 1645, 1590, 1510, 1460 (nujol), 1375 (nujol), 1300, 1260, 1230, 1180, 1150, 1060, 1025, 970, 890, 845, 815, 720 (nujol).

(d) an elemental analysis, after the sample has been previously dried at about 140° C. under inert atmosphere (%Δw=9.8), which indicated the following approximate percentage composition (average): carbon, 56.15%; hydrogen, 5.15%; nitrogen 6.30%; chlorine, 3.90%; oxygen (by difference), 28.50%

(e) a retention time (t$_R$) of 22.6 minutes when analyzed by reversed phase HPLC using a 5μ Zorbax ® ODS column, and eluting with a linear gradient from 0% to 50% solution B in solution A in 40 minutes (solution A: 25 mM NaH$_2$PO$_4$/acetonitrile (9/1) buffered at pH 6.0 with 0.1N NaOH; solution B: 25 mM NaH$_2$PO$_4$ /acetonitrile (3/7) buffered at pH 6.0 with 0.1N NaOH), with a flow rate of 2 ml/min.; (internal standard: 3,5-dihydroxytoluene $t_R$ 8.84 minutes)

Figure 6:
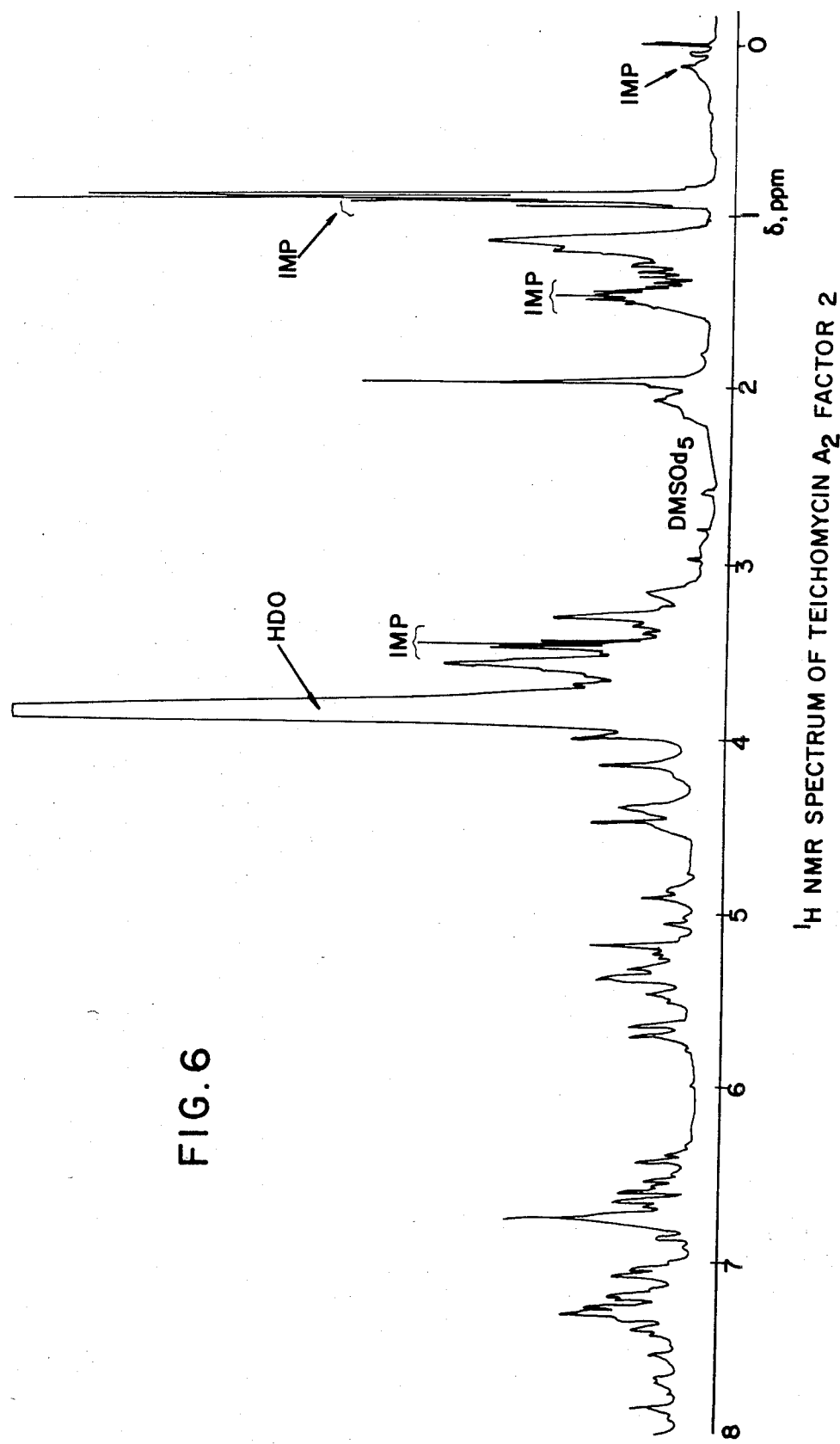

(f) the following groups of signals in 270 MHz $^1$H NMR spectrum (the entire spectrum is shown in FIG. 6 of the accompanying drawings) registered in DMSO-$d_6$ with the addition of a few drops of D$_2$O (conc. 25 mg/0.5 ml) (TMS as internal standard $\delta=0.00$ ppm): 0.7-1.5 (m); 1.8-2.2 (m); 2.7-4.5(m); 4.6-5.7 (m); 6.2-8.1 (m).

(g) an acidic function capable of forming salts.
(h) a salifiable basic function
(i) a molecular weight of about 1877 as determined by FAB mass spectrometry.

Figure 7:
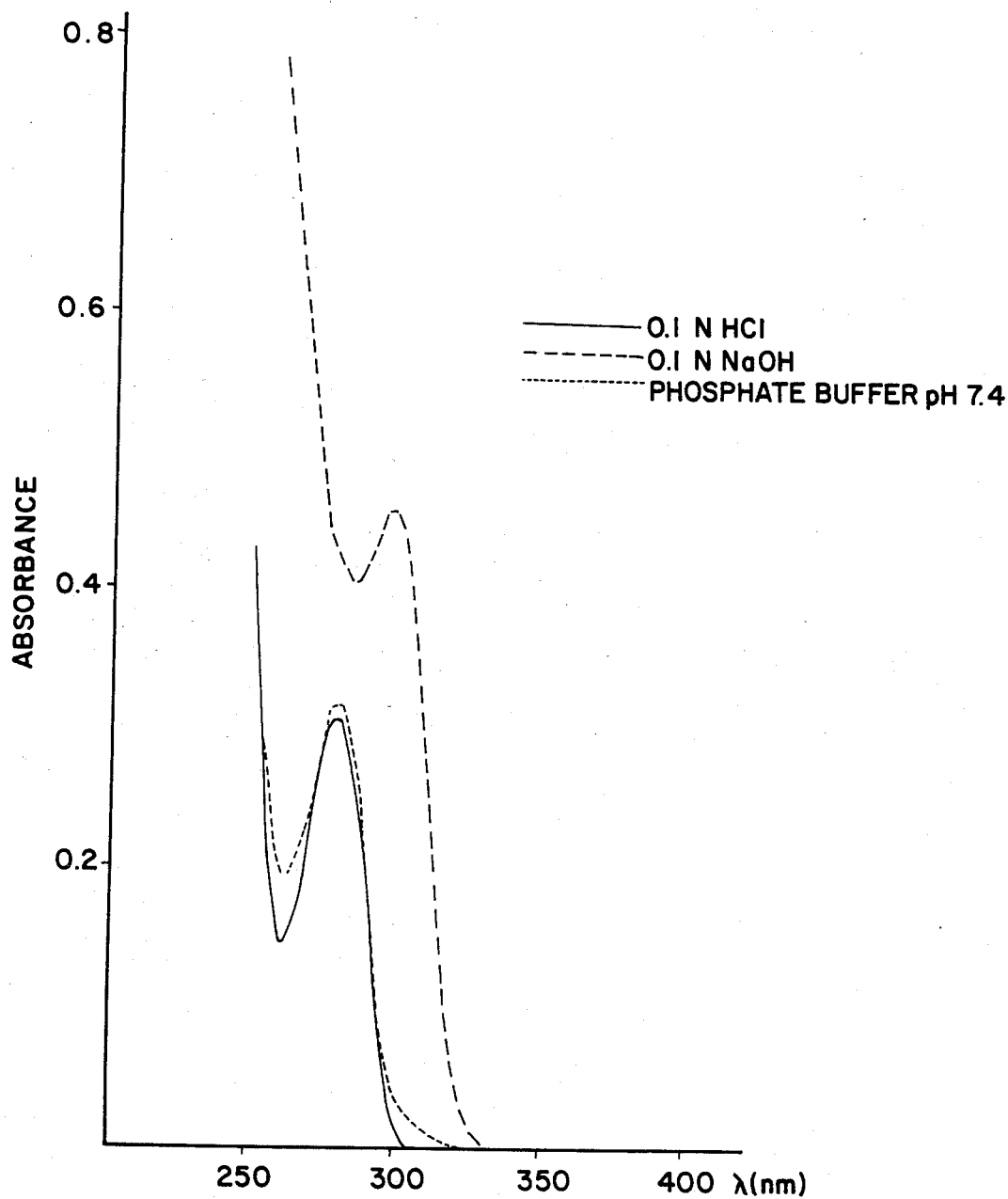

Teichomycin A$_2$ factor 3 is a white amorphous powder that, upon heating begins to decompose at 205° C. and is completely decomposed at 250° C., which has the following characteristcs:

(a) It is freely soluble in water at pH>7.0 or at pH<2, in dimethylformamide, dimethylsulfoxide, and propyleneglycol; slightly soluble in methylcellosolve and glycerol; poorly soluble in methanol and ethanol; almost insoluble in chloroform, benzene, n-hexane, acetonitrile, ethyl ether, acetone, ethyl acetate, carbon tetrachloride (b) an ultraviolet absorption spectrum, which is given in FIG. 7 of the accompanying drawings, that exhibits the following absorption maxima:

in 0.1N hydrochloric acid:

$\lambda_{max}$ 278 nm (E$_1$ $_{cm}$$^{1\%}$=49.2)

in phosphate buffer pH 7.4:

$\lambda_{max}$ 278 nm (E$_1$ $_{cm}$$^{1\%}$=50.8)

in 0.1N sodium hydroxide:

$\lambda_{max}$ 297 nm (E$_1$ $_{cm}$$^{1\%}$=72.7)

Figure 8:
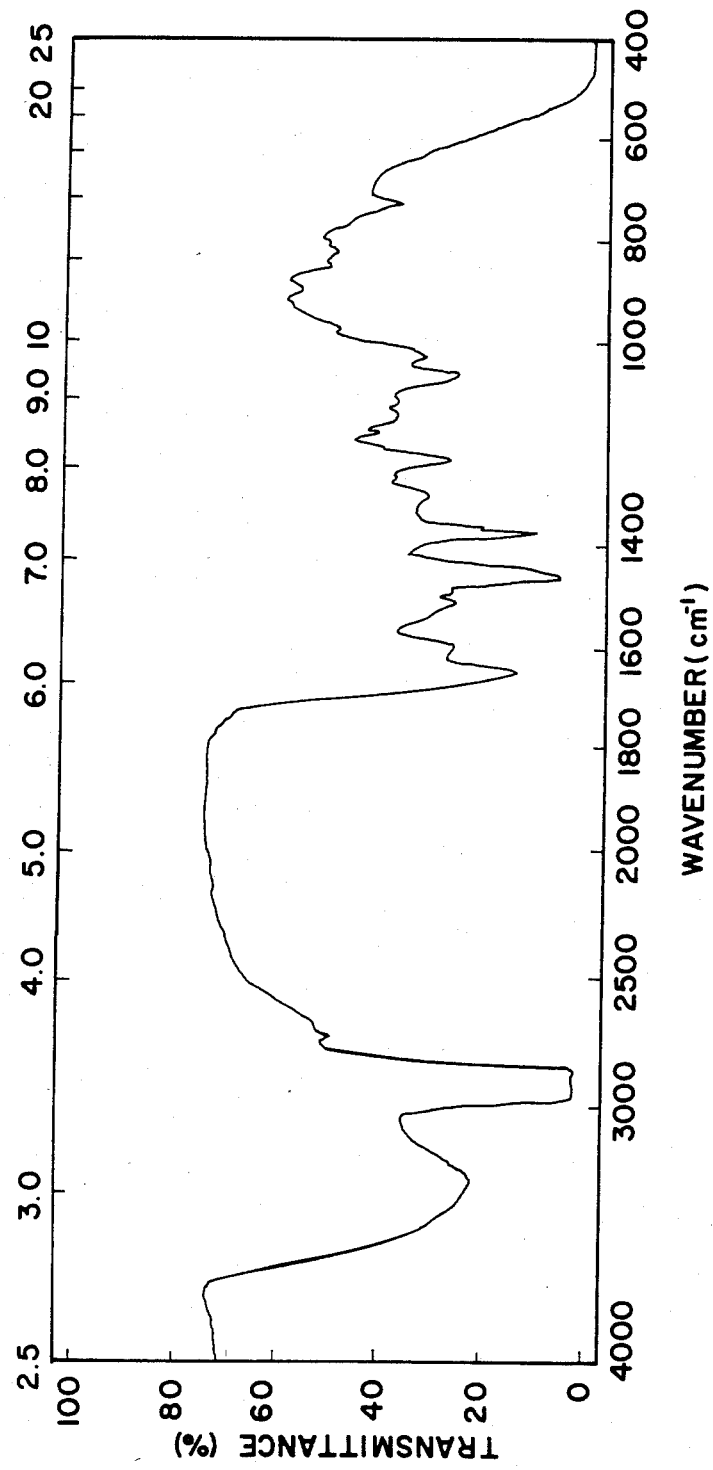

(c) an infrared absorption spectrum in nujol, shown in FIG. 8 of the accompanying drawings, with the following observable absorption maxima: 3700-3100, 2960-2850 (nujol); 1645, 1590, 1510, 1460 (nujol), 1375 (nujol); 1300, 1230, 1180, 1150, 1120, 1060, 1030, 970, 890, 845, 820, 800, 720 (nujol).

(d) an elemental analysis, after the sample has been previously dried at about 140° C. under inert atmosphere (% $\Delta w=12.0$) which indicated the following approximate percentage composition (average): carbon, 56.26%; hydrogen, 5.20%; nitrogen, 6.69%; chlorine, 3.95%; oxygen (by difference), 27.90%.

(e) a retention time ($t_R$) of 23.3 minutes when analyzed by reversed phase HPLC using a 5$\mu$ Zorbax ® ODS column and eluting with a linear gradient from 0% to 50% solution B in solution A in 40 minutes (solution A: 25 mM NaH$_2$PO$_4$/acetonitrile (9/1) buffered at pH 6.0 with 0.1N NaOH solution B: 25 mM NaH$_2$PO$_4$/acetonitrile (3/7) buffered at pH 6.0 with 0.1N NaOH), with a flow rate of 2 ml/min; (internal standard:3,5-dihydroxytoluene $t_R$ 8.84 minutes)

Figure 9:
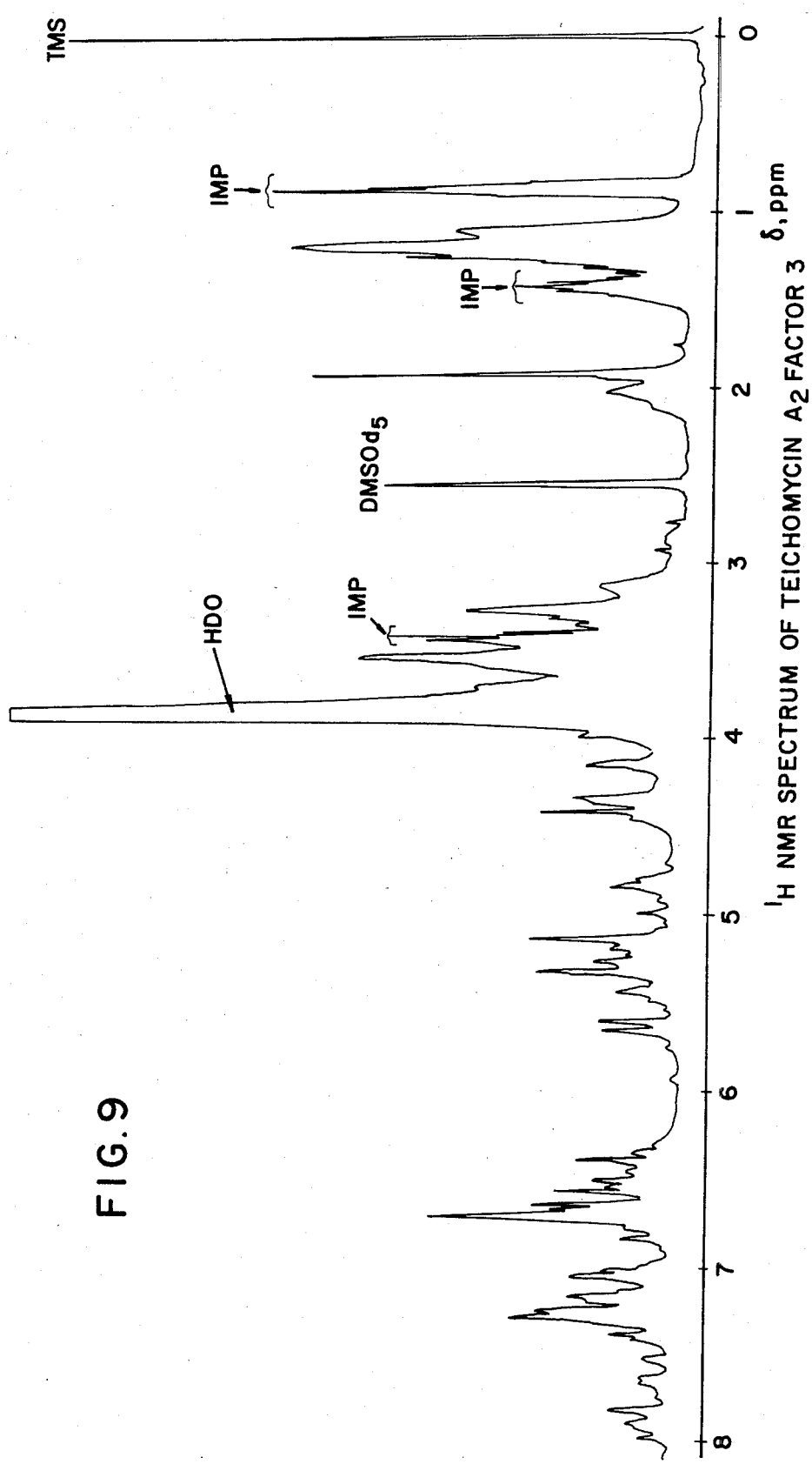

(f) the following groups of signals in 270 MHz $^1$H NMR spectrum (the entire spectrum is shown in FIG. 9 of the accompanying drawings) registered in DMSO-$d_6$ with the addition of a few drops of D$_2$O (conc. 25 mg/0.5 ml) (TMS as internal standard $\delta=0.00$ ppm): 0.7-1.5 (m); 1.8-2.0 (m); 2.7-4.5 (m); 4.6-5.7 (m); 6.2-8.0 (m).

(g) an acidic function capable of forming salts.
(h) a salifiable basic function
(i) a molecular weight of about 1877 as determined by FAB mass spectrometry.

Figure 10:
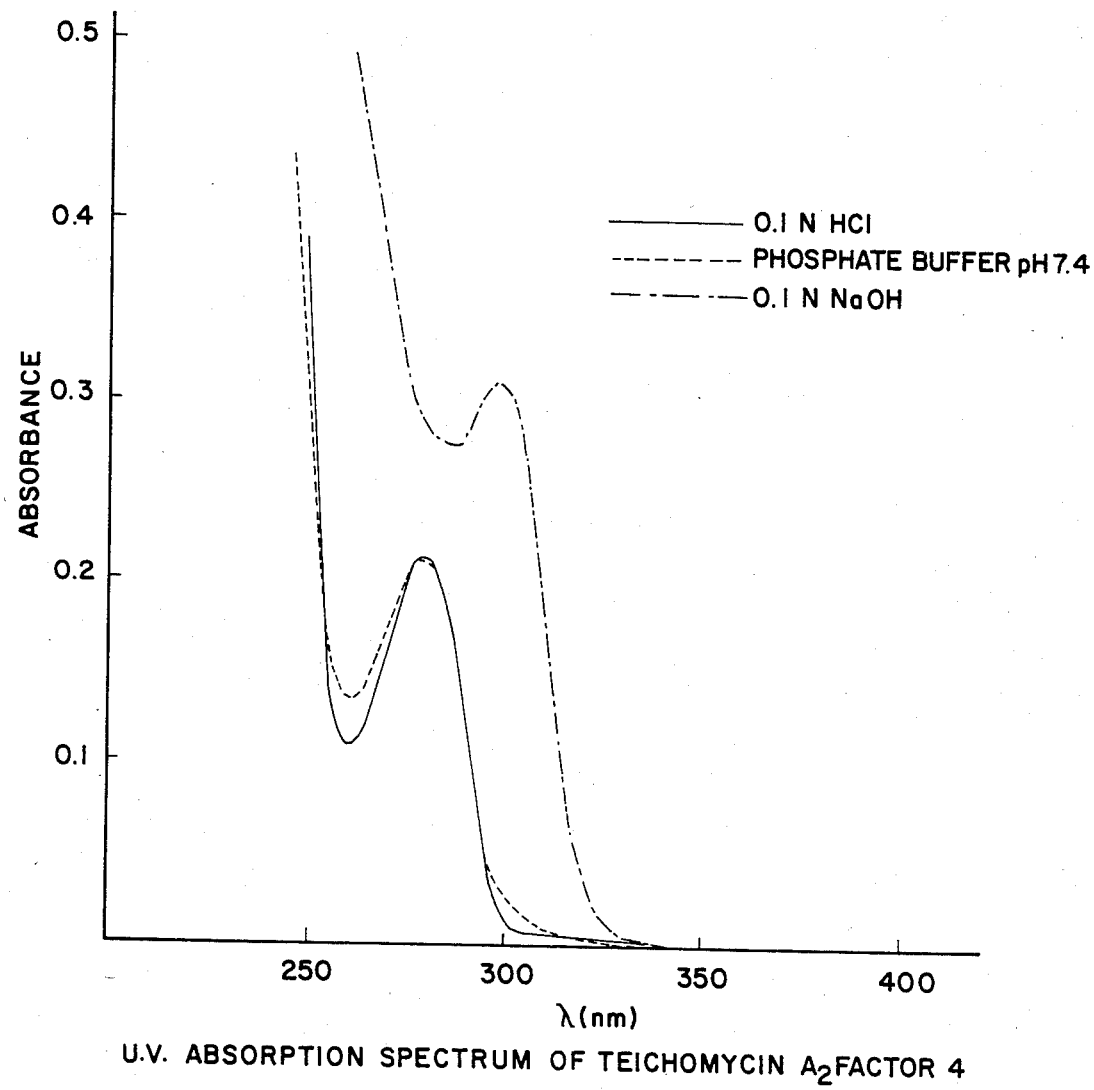

Teichomycin A$_2$ factor 4 is a white amorphous powder that upon heating, begins to darken at about 210° C. and is completely decomposed at 250° C., which has the following characteristics:

(a) It is freely soluble in water at pH>7.0 or at pH<2, in dimethylformamide, dimethylsulfoxide, and propyleneglycol; slightly soluble in methylcellosolve and glycerol; poorly soluble in methanol and ethanol, almost insoluble in chloroform, benzene, n-hexane, acetonitrile, ethyl ether, acetone, ethyl acetate, carbon tetrachloride (b) has an ultraviolet absorption spectrum, which is given in FIG. 10 of the accompanying drawings, that exhibits the following absorption maxima:

in 0.1 N hydrochloric acid $\lambda_{max}$ 278 nm (E$_1$ $_{cm}$$^{1\%}$=52.5)

in phosphate buffer pH 7.4:

$\lambda_{max}$ 278 nm (E$_1$ $_{cm}$$^{1\%}$=52.5)

in 0.1 N sodium hydroxide:

$\lambda_{max}$ 297 nm (E$_1$ $_{cm}$$^{1\%}$=75.5)

Figure 11:
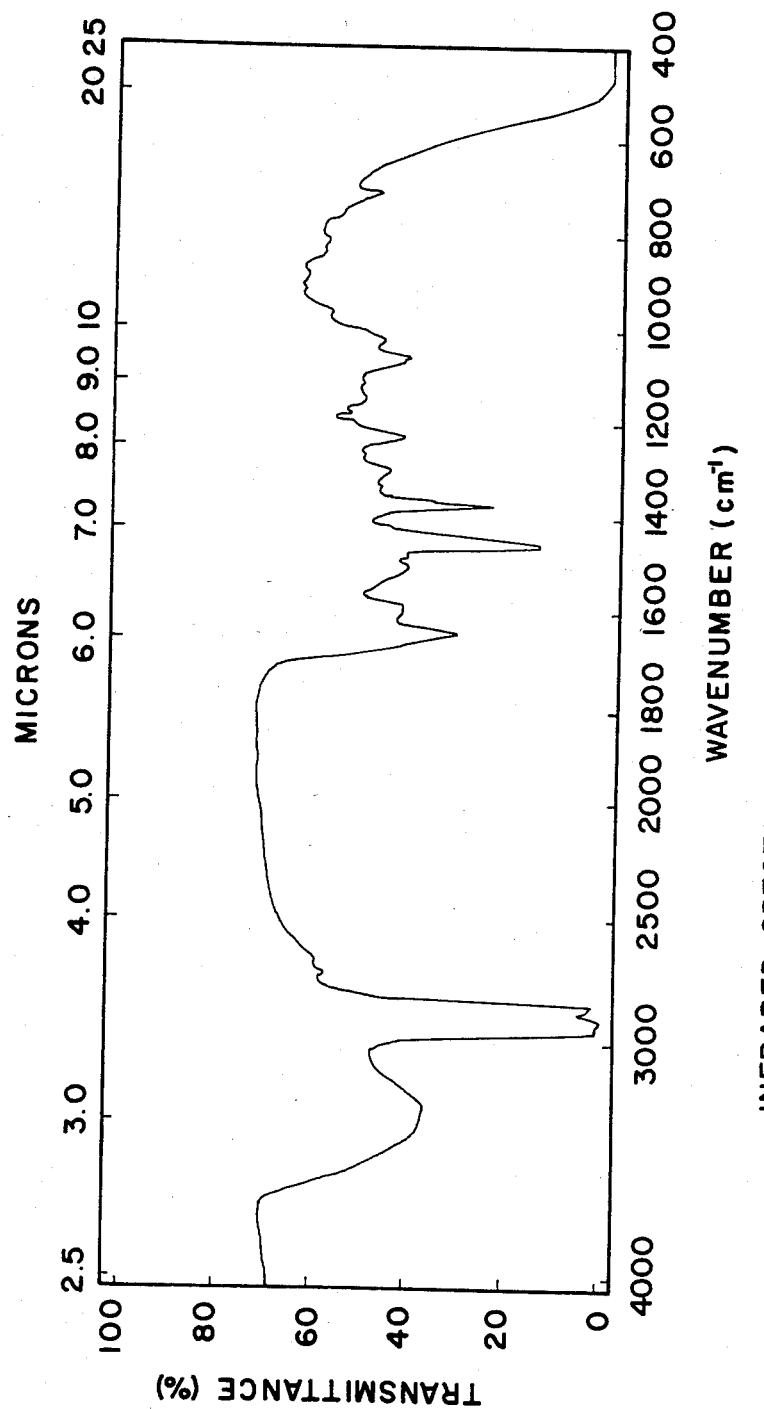

(c) an infrared absorption spectrum in nujol, shown in FIG. 11 of the accompanying drawings, with the following absorption maxima: 3700-3100, 2960-2840 (nujol), 1645, 1590, 1510, 1460 (nujol), 1375 (nujol), 1300, 1230, 1175, 1140, 1060, 1025, 970, 890, 840, 815, 720 (nujol);

(d) an elemental analysis, after the sample has been previously dried at about 140° C. under inert atmosphere (% $\Delta w=9.8$), which indicated the following approximate percentage composition (average): carbon 56.50%; hydrogen, 5.10%; nitrogen 6.50%; chlorine 3.80%; oxygen (by difference), 28.10%

(e) a retention time ($t_R$) of 25.8 minutes when analyzed by reversed phase HPLC using a 5$\mu$ Zorbax ® ODS column, and eluting with a linear gradient from 0% to 50% solution B in solution A in 40 minutes (solution A: 25 mM NaH$_2$PO$_4$/acetonitrile (9/1) buffered at pH 6.0 with 0.1N NaOH. solution B: 25 mM NaH$_2$PO$_4$/acetonitrile (3/7) buffered at pH 6.0 with 0.1N NaOH), with a flow rate of 2 ml/min.; (internal standard: 3,5-dihydroxy-toluene $t_R$ 8.84 minutes)

(f) an acidic function capable of forming salts.
(g) a salifiable basic function
(h) a molecular weight of about 1891 as determined by FAB mass spectrometry.

Figure 12:
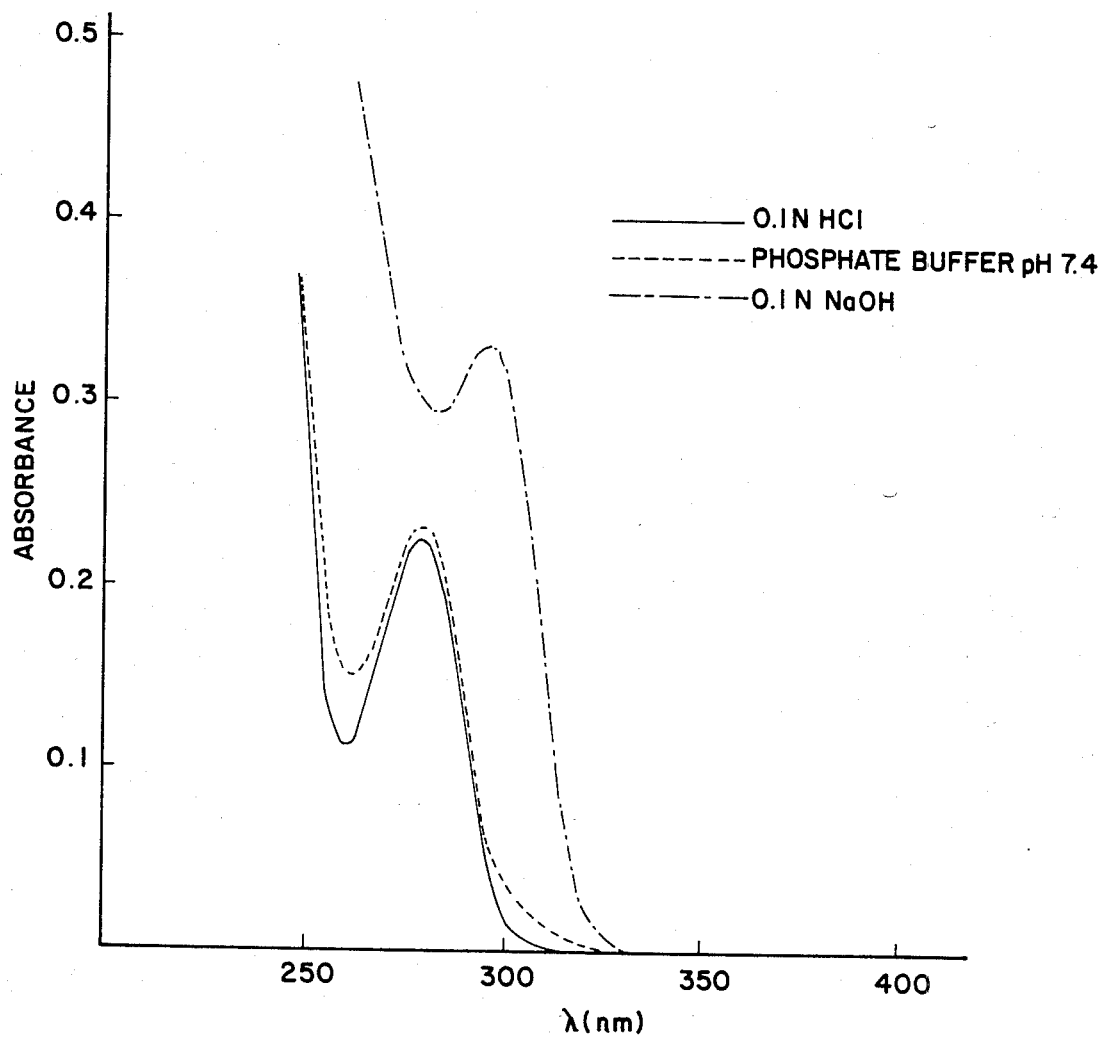

Teichomycin A$_2$ factor 5 is a white amorphous powder that commences to darken when heated to 210° C. and is completely decomposed at 250° C. which has the following characteristics:

(a) It is freely soluble in water at pH>7.0 or at pH<2 in dimethylformamide, dimethylsulfoxide and propyleneglycol; slightly soluble in methylcellosolve and glycerol; poorly soluble in methanol and ethanol; almost insoluble in chloroform, benzene, n-hexane, acetonitrile, ethyl ether, acetone, ethyl acetate, carbon tetrachloride (b) It has an ultraviolet absorption spectrum, which is given in FIG. 12 of the accompanying drawings, that exhibits the following absorption maxima:

in 0.1 N hydrochloric acid:

$\lambda_{max}$ 278 nm ($E_{1\ cm}^{1\%}$ = 49.6)

in phosphate buffer pH 7.4:

$\lambda_{max}$ 278 nm ($e_{1\ cm}^{1\%}$ = 51.8)

in 0.1 N sodium hydroxide:

$\lambda_{max}$ 297 nm ($E_{1\ cm}^{1\%}$ = 78.8)

Figure 13:
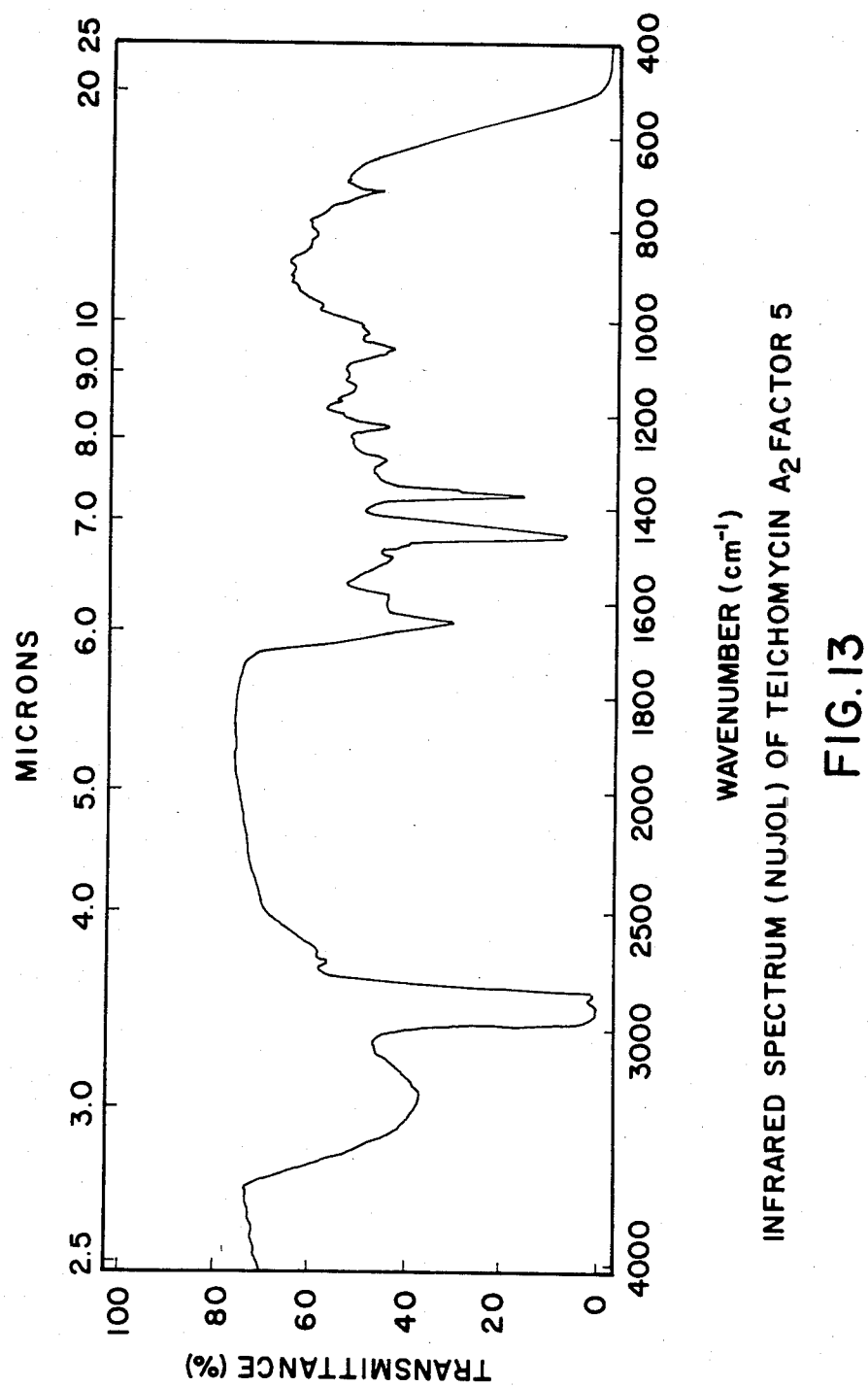

(c) an infrared absorption spectrum in nujol, shown in FIG. 13 of the accompanying drawings, with the following observable absorption maxima: 3700–3100, 2960–2840 (nujol), 1645, 1590, 1510, 1460 (nujol), 1375 (nujol), 1300, 1230, 1175, 1145, 1060, 1025, 970, 890, 840, 815, 720 (nujol).

(d) an elemental analysis, after the sample has been previously dried at about 140° C. under inert atmosphere (%Δw=10.1), which indicated the following approximate percentage composition (average): carbon, 56.60%; hydrogen, 5.05%; nitrogen 6.63%; chlorine, 3.85%; oxygen (by difference), 27.87%

(e) a retention time ($t_R$) of 26.4 minutes when analyzed by reversed phase HPLC using a 5μ Zorbax ® ODS column, and eluting with a linear gradient from 0% to 50% solution B in solution A in 40 minutes (solution A: 25 mM NaH$_2$PO$_4$/acetonitrile (9/1) buffered at pH 6.0 with 0.1N NaOH; solution B: 25 mM NaH$_2$PO$_4$/acetonitrile (3/7) buffered at pH 6.0 with 0.1N NaOH), with a flow rate of 2 ml/min.; (internal standard: 3,5-dihydroxytoluene $t_R$ 8.84 minutes)

(f) an acidic function capable of forming salts.

(g) a salifiable basic function (h) a molecular weight of about 1891 as determined by FAB mass spectrometry.

Each of Teichomycin A$_2$ factors 1,2,3,4 and 5 contains an acidic function which is capable of forming salts. The alkali metal, alkaline earth metal, and pharmaceutically acceptable ammonium salts of Teichomycin A$_2$ factors 1,2,3,4 and 5 represent a further specific object of the present invention.

Representative alkali metal and alkaline earth metal salts include sodium, potassium, lithium, calcium, and magnesium salts. The ammonium salts include ammonium and primary, secondary or tertiary (C$_1$-C$_4$)alkylammonium and hydroxy-(C$_1$-C$_4$)alkylammonium salts.

The alkali and alkaline earth metal salts are prepared according to the usual procedures commonly employed for preparing metal salts. As an example, Teichomycin A$_2$ factor 1,2,3,4 or 5 in the free acidic form is dissolved into a suitable solvent such as propylene glycol and about the stoichiometric amount of a suitable selected mineral base is gradually added to the obtained solution.

The alkali or alkaline earth metal salt which forms is then recovered by precipitation with a non-solvent and filtration.

Alternatively these salts can be prepared in a substantially anhydrous form through lyophilization; in this case aqueous solutions containing the desired salts, resulting from the salification of the free acidic form with a suitably selected alkali or alkaline earth metal carbonate or hydroxide in such a quantity as to obtain a pH between 7 and 8 are filtered from any insoluble and lyophilized.

The organic ammonium salts can be prepared either by adding the properly selected amine to a solution of the free acidic form of Teichomycin A$_2$ factors 1,2,3,4 and 5 in a suitable solvent such as propylene glycol, and then evaporating off the solvent and the excess of the amine reagent or alternatively contacting the two reagents in the minimum amount of water and then precipitating the obtained salts by the addition of a non-solvent.

As stated before, each of Teichomycin A$_2$ factors 1,2,3,4 and 5 contains also a basic function capable of being salified. Their pharmaceutically acceptable acid addition salts, prepared as known per se in the art, by contacting the pure single factors with a rather strong acid, preferably with a mineral acid, represent a further specific object of the present invention.

PREPARATION OF TEICHOMYCIN A$_2$ FACTOR 2 SODIUM SALT

An aqueous solution of Teichomycin A$_2$ factor 2 (150 mg, 15 ml) is brought to pH 8.0 by the dropwise addition of 0.1 N NaOH. The obtained solution is filtered, transferred into the chamber of a freeze-drying system and frozen. After freezing is complete, the chamber is evacuated to 0.1 Torr and ice is sublimated by bringing the heating plate to 0° C. The process continues until the product is almost dry (about 1% moisture). Titration of a solution of Teichomycin A$_2$ factor 2 sodium salt thus obtained in 25 ml methylcellosolve/H$_2$O 3/1 with 0.1 N HCl evidences the presence of two titratable functions characterized by the following pK: 7.03 and 4.78.

By following the procedure described above but starting from Teichomycin A$_2$ factors 1,3,4 and 5 the corresponding sodium salts are obtained. Determination of the amount of sodium in the end salts confirms the formation of a monosodium salt.

The in vitro antibacterial activity of Teichomycin A$_2$ factors 1,2,3,4 and 5, which showed to be mainly active against Gram-positive bacteria, was determined against clinical isolates of staphylococci and streptococci using two-fold dilution method in microtiter system. Penassay broth (Difco) and Todd-Hewitt broth (Difco) were used for staphylococci and streptococci respectively. Overnight broth cultures were diluted so that the final inoculum was about 10$^3$ colony forming units/ml. Minimal inhibitory concentration (MIC) was read as the lowest concentration which showed no visible growth after 18–24 h incubation at 37° C. The obtained results are summarized in TABLE II below:

TABLE II

| | In vitro antibacterial activity of Teichomycin A$_2$ factors 1, 2, 3, 4 and 5 | | | | | |
|---|---|---|---|---|---|---|
| | No. of | M.I.C. (μg/ml) | | | | |
| Microorganism | tested strains | Teichomycin A$_2$ factor 1 | Teichomycin A$_2$ factor 2 | Teichomycin A$_2$ factor 3 | Teichomycin A$_2$ factor 4 | Teichomycin A$_2$ factor 5 |
| *Staphylococcus aureus* | 5 | 0.8–1.6 | 0.8–1.6 | 0.4–0.8 | 0.2–0.8 | 0.2–0.8 |

TABLE II-continued

| | | In vitro antibacterial activity of Teichomycin $A_2$ factors 1, 2, 3, 4 and 5 | | | | |
|---|---|---|---|---|---|---|
| | No. of | M.I.C. ($\mu$g/ml) | | | | |
| Microorganism | tested strains | Teichomycin $A_2$ factor 1 | Teichomycin $A_2$ factor 2 | Teichomycin $A_2$ factor 3 | Teichomycin $A_2$ factor 4 | Teichomycin $A_2$ factor 5 |
| Staphylococcus epidermidis | 4 | 0.2–1.6 | 0.1–1.6 | 0.2–0.8 | 0.2–0.8 | 0.2–0.8 |
| Streptococcus pyogenes | 7 | 0.05–0.1 | 0.025–0.1 | 0.025–0.05 | 0.006–0.05 | 0.006–0.05 |
| Streptococcus pneumoniae | 6 | 0.1–0.2 | 0.05–0.1 | 0.05–0.1 | 0.05–0.1 | 0.05–0.1 |
| Streptococcus faecalis | 5 | 0.2–0.4 | 0.1–0.4 | 0.1–0.2 | 0.1–0.4 | 0.1–0.4 |
| Streptococcus mitis | 1 | 0.025 | 0.025 | 0.0125 | 0.025 | 0.025 |
| Streptococcus salivarius | 1 | 0.2 | 0.2 | 0.1 | 0.05 | 0.05 |
| Streptococcus sanguis | 1 | 0.1 | 0.1 | 0.1 | 0.05 | 0.05 |
| Streptococcus bovis | 1 | 0.4 | 0.4 | 0.2 | 0.4 | 0.4 |
| Streptococcus agalactiae | 1 | 0.1 | 0.1 | 0.05 | 0.1 | 0.1 |

The relationship of microbiological potency of the individual factors 1,2,3,4 and 5 was determined by the agar diffusion method using *S. aureus* ATCC 6538 as germ test, and Teichomycin $A_2$ complex as standard. In particular an adequate amount of Teichomycin $A_2$ factor 1, Teichomycin $A_2$ factor 2, Teichomycin $A_2$ factor 3, Teichomycin $A_2$ factor 4, Teichomycin $A_2$ factor 5 and Teichomycin $A_2$ complex used as the standard is dissolved in dimethylformamide at a concentration of 2000 $\mu$g/ml. These solutions are further diluted using phosphate buffer 0.067 M pH 7.4 supplemented with 1% bovine serum in order to provide the following concentrations: 2.5, 5, 10, and 20 $\mu$g/ml.

Filter paper discs are then soaked into the sample solutions and placed at regular intervals on the surface of agar plates seeded with a suspension of the test microorganism. The plates are incubated at 37° C. for 18 hours and then the diameter of the inhibition zones are measured. The data obtained are fed into a computer to calculate the potency of the individual factors relative to the complex.

The results obtained are reported herein below

| Teichomycin $A_2$ factor 1 | 841 U/mg |
|---|---|
| Teichomycin $A_2$ factor 2 | 1086 U/mg |
| Teichomycin $A_2$ factor 3 | 1131 U/mg |
| Teichomycin $A_2$ factor 4 | 1066 U/mg |
| Teichomycin $A_2$ factor 5 | 954 U/mg |
| Teichomycin $A_2$ complex | 1000 U/mg |

Teichomycin $A_2$ factors 2,3,4 and 5 were tested in the experimental infections caused by *S. pneumoniae* and by *S. pyogenes* in mice. The experiments were carried out in comparison with Teichomycin $A_2$ complex. The results obtained are reported in Table III below

TABLE III

| | In vivo antibacterial activity | |
|---|---|---|
| | $ED_{50}$ (mg/kg/day) s.c. | |
| Compound | S. pneumoniae L 44 | S. pyogenes L 49 |
| Teichomycin $A_2$ factor 2 | 0.28 (0.22–0.34) | 0.15 (0.13–0.18) |
| Teichomycin $A_2$ factor 3 | 0.27 (0.23–0.32) | 0.13 (0.11–0.16) |
| Teichomycin $A_2$ factor 4 | 0.12 (0.98–0.14) | 0.098 – (0.073–0.11) |
| Teichomycin $A_2$ factor 5 | 0.13 (0.10–0.15) | 0.10 (0.098–0.13) |
| Teichomycin $A_2$ complex | 0.35 (0.28–0.44) | 0.18 (—) |

The approximate acute toxicity in mice (i.p.) for Teichomycin $A_2$ factors 1,2,3,4 and 5 is as shown in Table IV below:

TABLE IV

| Acute toxicity in mice (i.p.) | |
|---|---|
| Compound | Approximate $LD_{50}$ (mg/kg) |
| Teichomycin $A_2$ factor 1 | >1500 < 2000 |
| Teichomycin $A_2$ factor 2 | >1500 < 2000 |
| Teichomycin $A_2$ factor 3 | >1000 < 1500 |
| Teichomycin $A_2$ factor 4 | >500 < 1000 |
| Teichomycin $A_2$ factor 5 | >500 < 1000 |

In view of the above, the compounds of the present invention, Teichomycin $A_2$ factors 1, Teichomycin $A_2$ factor 2, Teichomycin $A_2$ factor 3, Teichomycin $A_2$ factor 4 and Teichomycin $A_2$ factor 5 can effectively be employed as the active ingredient of antimicrobial preparations used in human and veterinary medicine for the prevention and treatment of infectious diseases caused by pathogenic bacteria which are susceptible to the active ingredients. In such treatments these compounds may be employed as such or used as single individual factors or, considering the similarity of their activity pattern, also in the form of mixtures of two or more of the five factors in any proportion.

The compounds of the present invention can be administered orally, topically or parenterally wherein however parenteral administration is most preferred. Depending on the route of administration, these compounds can be formulated into various dosage forms. Preparations for oral administration may be in the form of capsules, tablets, liquid solutions or suspension. As known in the art the capsules and tablets may contain in addition to the active ingredient, conventional excipients such as diluents, e.g. lactose, calcium phosphate, sorbitol and the like, lubricants, e.g. magnesium stearate, talc, polyethylene glycol, binding agents, e.g. polyvinylpyrrolidone, gelatin, sorbitol, tragacanth, acacia, flavoring agents, and acceptable disintegrating and wetting agents. The liquid preparations generally in the form of aqueous or oily solutions or suspensions, may contain conventional additives such as suspending agents. For topical use the compounds of the present invention may also be prepared in suitable forms for absorption through the skin, the mucous membranes of the nose and throat or the bronchial tissues and may conveniently take the form of liquid sprays or inhalants, lozenges, or throat paints. For medication of the eyes or ears, the preparation may be presented in liquid or semiliquid form. Topical applications may be formulated in hydrophobic or hydrophilic bases as ointments, creams, lotions, paints, or powders.

Compositions for injection may take such forms as suspensions, solutions, or emulsions in oily or aqueous vehicles, and may contain formulatory agents such as suspending, stabilizing and/or dispersing agents. Alternatively, the active ingredient may be in powder form for reconstitution, at the time of delivery, with a suitable vehicle, such as sterile water. The amount of active principle to be administered depends on various factors such as the size and condition of the subject to be treated, the route and frequency of administration, and the causative agent involved. Teichomycin A$_2$ factors 1, 2, 3, 4 and 5 are generally effective at a daily dosage comprised between about 0.1 and about 20 mg of active ingredient per Kg of body weight, optionally divided in 2 administrations per day. Particularly desirable compositions are those prepared in the form of dosage units containing from about 50 to about 250 mg per unit.

Representative examples of preparation of pharmaceutical compositions are as follows:

A parenteral solution is prepared with
100 mg of Teichomycin A$_2$ factor 2 sodium salt dissolved in 2 ml of sterile water for injection
A parenteral solution is prepared with
250 mg of Teichomycin A$_2$ factor 3 sodium salt dissolved in 3 ml of sterile water for injection
A topical ointment is prepared with
200 mg of Teichomycin A$_2$ factor 2
600 mg of polyethylene glycol 4000 U.S.P.
1.2 g of polyethylene glycol 400 U.S.P.

Besides their activity as medicaments, the compounds of the present invention can be used as animal growth promoters.

For this purpose, one or more of the compounds of the invention is administered orally in a suitable feed. The exact concentration employed is that which is required to provide for the active agent in a growth promotant effective amount when normal amounts of feed are consumed.

The addition of the active compounds of the invention to animal feed is preferably accomplished by preparing an appropriate feed premix containing the active compounds in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and Co., S. Francisco, USA, 1969 or "Livestock Feeds and Feeding", O and B Books, Corvallis, Ore., USA, 1977) and are incorporated herein by reference.

We claim:
1. An essentially pure individual antibiotic compound selected from the group consisting of Teichomycin A$_2$ factor 1, Teichomycin A$_2$ factor 2, Teichomycin A$_2$ factor 3, Teichomycin A$_2$ factor 4, Teichomycin A$_2$ factor 5, identified respectively by the following chemico-physical characteristics:

Teichomycin A$_2$ factor 1: a white amorphous powder that upon heating begins to darken at about 220° C. and is completely decomposed at 255° C., which
(a) is freely soluble in water at pH >7.0 or at pH <2, in dimethylformamide, dimethylsulfoxide, and propyleneglycol; slightly soluble in methylcellosolve and glycerol; poorly soluble in methanol and ethanol, almost insoluble in chloroform, benzene, n-hexane, acetonitrile, ethyl ether, acetone, ethyl acetate, carbon tetrachloride
(b) has an ultraviolet absorption spectrum that exhibits the following absorption maxima:
in 0.1N hydrochloric acid:

$\lambda_{max}$ 278 nm ($E^{1\%}{}_{1cm}$ =49.5)

in phosphate buffer pH 7.4 :

$\lambda$278 nm ($E^{1\%}{}_{1cm}$ =50.0)

in 0.1N sodium hydroxide :

$\lambda_{max}$ 297 nm ($E^{1\%}{}_{1cm}$ =72.1)

(c) an infrared absorption spectrum in nujol with the following absorption maxima: 3700–3100, 2960–2840 (nujol), 1645, 1590, 1510, 1460 (nujol), 1375 (nujol), 1305, 1230, 1180, 1155, 1060, 1025, 970, 890, 845, 815, 720 (nujol);
(d) an elemental analysis, after the sample has been previously dried at about 140° C. under inert atmosphere (%$\Delta$w = 8.5), which indicated the following approximate percentage composition (average): carbon 56.70%; hydrogen, 4.90%; nitrogen 6.65%; chlorine 3.80%; oxygen (by difference), 27.95%
(e) a retention time ($t_R$) of 21.2 minutes when analyzed by reversed phase HPLC using a 5$\mu$ Zorbax ® ODS column, and eluting with a linear gradient from 0% to 50% solution B in solution A in 40 minutes (solution A: 25 mM NaH$_2$PO$_4$/acetonitrile (9/1) buffered at pH 6.0 with 0.1N NaOH; solution B: 25 mM NaH$_2$PO$_4$/acetonitrile (3/7) buffered at pH 6.0 with 0.1N NaOH), with a flow rate of 2 ml/min.; (internal standard: 3,5-dihydroxy-toluene $t_R$ 8.84 minutes)
(f) the following groups of signals in the 270 MHz $^1$H NMR spectrum registered in DMSO-d$_6$ with the addition of a few drops of D$_2$O (conc. 25 mg/0.5 ml) (TMS as internal standard: $\delta$=0.00 ppm): 0.8–1.5(m); 1.7–2.3 (m); 2.7–4.0 (m); 4.0–4.7 (m) 4.8–5.8 (m); 6.2–8.1 (m)
(g) an acidic function capable of forming salts;
(h) a salifiable basic function
(i) a molecular weight of about 1875 as determined by FAB mass spectrometry;

Teichomycin A$_2$ factor 2: a white amorphous powder that commences to darken when heated to 210° C. and is completely decomposed at 250° C., which
(a) is freely soluble in water at pH >7.0 or at pH <2 in dimethylformamide, dimethylsulfoxide and propyleneglycol; slightly soluble in methylcellosolve and glycerol; poorly soluble in methanol and ethanol; almost insoluble in chloroform, benzene, n-hexane, acetonitrile, ethyl ether, acetone, ethyl acetate, carbon tetrachloride
(b) has an ultraviolet absorption spectrum that exhibits the following absorption maxima:
in 0.1N hydrochloric acid:

$\lambda_{max}$ 278 nm ($E^{1\%}{}_{1cm}$ =48)

in phosphate buffer pH 7.4:

$\lambda_{max}$ 278 nm ($E^{1\%}{}_{1cm}$ =49.0)

in 0.1N sodium hydroxide:

$\lambda_{max}$ 297 nm ($E^{1\%}{}_{1cm}$ =70.0)

(c) an infrared absorption spectrum in nujol with the following observable absorption maxima: 3700–3100, 2960–2860 (nujol), 1645, 1590, 1510, 1460 (nujol), 1375 (nujol), 1300, 1260, 1230, 1180, 1150, 1060, 1025, 970, 890, 845, 815, 720 (nujol);

(d) an elemental analysis, after the sample has been previously dried at about 140° C. under inert atmosphere (%Δw =9.8), which indicated the following approximate percentage composition (average): carbon, 56.15%; hydrogen, 5.15%; nitrogen 6.30%; chlorine, 3.90%; oxygen (by difference), 28.50%

(e) a retention time ($t_R$) of 22.6 minutes when analyzed by reversed phase HPLC using a 5μ Zorbax ® ODS column, and eluting with a linear gradient from 0% to 50% solution B in solution A in 40 minutes (solution A: 25 mM NaH$_2$PO$_4$/acetonitrile (9/1) buffered at pH 6.0 with 0.1N NaOH solution B: 25 mM NaH$_2$PO$_4$/acetonitrile (3/7) buffered at pH 6.0 with 0.1N NaOH), with a flow rate of 2 ml/min.; (internal standard: 3,5-dihydroxytoluene $t_R$ 8.84 minutes)

(f) the following groups of signals in 270 MHz $^1$H NMR spectrum registered in DMSO-d$_6$ with the addition of a few drops of D$_2$O (conc. 25 mg/0.5C ml) (TMS as internal standard δ=0.00 ppm): 0.7–1.5 (m); 1.8–2.2 (m); 2.7–4.5(m); 4.6–5.7 (m); 6.2–8.1 (m).

(g) an acidic function capable of forming salts;
(h) a salifiable basic function
(i) a molecular weight of about 1877 as determined by FAB mass spectrometry;

Teichomycin A$_2$ factor 3: a white amorphous powder that, upon heating begins to decompose at 205° C. and is completely decomposed at 250° C., which
(a) is freely soluble in water at pH >7.0 or at pH <2, in dimethylformamide, dimethylsulfoxide, and propyleneglycol;
slightly soluble in methylcellosolve and glycerol; poorly soluble in methanol and ethanol; almost insoluble in chloroform, benzene, n-hexane, acetonitrile, ethyl ether, acetone, ethyl acetate, carbon tetrachloride
(b) an ultraviolet absorption spectrum that exhibits the following absorption maxima:
in 0.1N hydrochloric acid:

$\lambda_{max}$ 278 nm ($E^{1\%}{}_{1cm}$ =49.2)

in phosphate buffer pH 7.4:

$\lambda_{max}$ 278 nm ($E^{1\%}{}_{1cm}$ =50.8)

in 0.1N sodium hydroxide:

$\lambda_{max}$ 297 nm ($E^{1\%}{}_{1cm}$ =72.7)

(c) an infrared absorption spectrum in nujol with the following observable absorption maxima: 3700–3100, 2960–2850 (nujoln); 1645, 1590, 1510, 1460 (nujol), 1375 (nujol); 1300, 1230, 1180, 1150, 1120, 1060, 1030, 970, 890, 845, 820, 800, 720 (nujol);

(d) an elemental analysis, after the sample has been previously dried at about 140° C. under inert atmosphere (%Δw = 12.0) which indicated the following approximate percentage composition (average): carbon, 56.26%; hydrogen, 5.20%; nitrogen, 6.69%; chlorine, 3.95%; oxygen (by difference), 27.90%, (e) a retention time ($t_R$) of 23.3 minutes when analyzed by reversed phase HPLC using a 5μ Zorbax ® ODS column and eluting with a linear gradient from 0% to 50% solution B in solution A in 40 minutes (solution A: 25 mM NaH$_2$PO$_4$/acetonitrile (9/1) buffered at pH 6.0 with 0.1N NaOH
solution B: 25 mM NaH$_2$PO$_4$/acetonitrile (3/7) buffered at pH 6.0 with 0.1N NaOH), with a flow rate of 2 ml/min; (internal standard:3,5-dihydroxytoluene $t_R$ 8.84 minutes)

(f) the following groups of signals in 270 MHz $^1$H NMR spectrum registered in DMSO-d$_6$ with the addition of a few drops of D$_2$O (conc. 25 mg/0.5 ml) (TMS as internal standard δ=0.00 ppm): 0.7–1.5 (m); 1.8–2.0 (m); 2.7–4.5 (m); 4.6–5.7 (m); 6.2–8.0 (m);

(g) an acidic function capable of forming salts.
(h) a salifiable basic function
(i) a molecular weight of about 1877 as determined by FAB mass spectrometry;

Teichomycin A$_2$ factor 4: a white amorphous powder that upon heating, begins to darken at about 210° C. and is completely decomposed at 250° C., which
(a) is freely soluble in water at pH >7.0 or at pH <2, in dimethylformamide, dimethylsulfoxide, and propyleneglycol;
slightly soluble in methylcellosolve and glycerol; poorly soluble in methanol and ethanol, almost insoluble in chloroform, benzene, n-hexane, acetonitrile, ethyl ether, acetone, ethyl acetate, carbon tetrachloride
(b) has an ultraviolet absorption spectrum that exhibits the following absorption maxima:
in 0.1N hydrochloric acid :

$\lambda_{max}$ 278 nm ($E^{1\%}{}_{1cm}$ =52.5)

in phosphate buffer pH 7.4 :

$\lambda_{max}$ 278 nm ($E^{1\%}{}_{1cm}$ =52.5)

in 0.1N sodium hydroxide :

$\lambda_{max}$ 297 nm ($E^{1\%}{}_{1cm}$ =75.5)

(c) an infrared absorption spectrum in nujol with the following absorption maxima: 3700–3100, 2960–2840 (nujol), 1645, 1590, 1510, 1460 (nujol), 1375 (nujol), 1300, 1230, 1175, 1140, 1060, 1025, 970, 890, 840, 815, 720 (nujol);

(d) an elemental analysis, after the sample has been previously dried at about 140° C. under inert atmosphere (%Δw = 9.8), which indicated the following approximate percentage composition (average): carbon 56.50%; hydrogen, 5.10%; nitrogen 6.50%; chlorine 3.80%; oxygen (by difference), 28.10%

(e) a retention time ($t_R$) of 25.8 minutes when analyzed by reversed phase HPLC using a 5μ ® Zorbax ODS column, and eluting with a linear gradient from 0% to 50% solution B in solution A in 40 minutes
(solution A: 25 mM NaH$_2$PO$_4$/acetonitrile (9/1) buffered at pH 6.0 with 0.1N NaOH;
solution B: 25 mM NaH$_2$PO$_4$/acetonitrile (3/7) buffered at pH 6.0 with 0.1N NaOH), with a flow rate of 2 ml/min.; (internal standard: 3,5-dihydroxy-toluene $t_R$ 8.84 minutes)

(f) an acidic function capable of forming salts (g) a salifiable basic function (h) a molecular weight of about 1891 as determined by FAB mass spectrometry Teichomycin A₂ factor 5: a white amorphous powder that commences to darken when heated to 210° C. and is completely decomposed at 250° C., which (a) is freely soluble in water at pH >7.0 or at pH <2 in dimethylformamide, dimethylsulfoxide and propyleneglycol;

slightly soluble in methylcellosolve and glycerol;

poorly soluble in methanol and ethanol; almost insoluble in chloroform, benzene, n-hexane, acetonitrile, ethyl ether, acetone, ethyl acetate, carbon tetrachloride (b) has an ultraviolet absorption spectrum that exhibits the following absorption maxima:

in 0.1N hydrochloric acid:

$\lambda_{max}$ 278 nm ($E^{1\%}_{1cm}$ =49.6)

in phosphate buffer pH 7.4:

$\lambda_{max}$ 278 nm ($E^{1\%}_{1cm}$ =51.8)

in 0.1N sodium hydroxide:

$\lambda_{max}$ 297 nm ($E^{1\%}_{1cm}$ =78.8)

(c) an infrared absorption spectrum in nujol with the following observable absorption maxima: 3700–3100, 2960–2840 (nujol), 1645, 1590, 1510, 1460 (nujol), 1375 (nujol), 1300, 1230, 1175, 1145, 1060, 1025, 970, 890, 840, 815, 720 (nujol), (d) an elemental analysis, after the sample has been previously dried at about 140° C. under inert atmosphere (%Δw =10.1), which indicated the following approximate percentage composition (average): carbon, 56,60%; hydrogen, 5.05%; nitrogen 6.63%; chlorine, 3.85%; oxygen (by difference), 27.87%

(e) a retention time ($t_R$) of 26.4 minutes when analyzed by reversed phase HPLC using a 5μ Zorbax ® ODS column, and eluting with a linear gradient from 0% to 50% solution B in solution A in 40 minutes (solution A: 25 mM NaH₂PO₄/acetonitrile (9/1) buffered at pH 6.0 with 0.1N NaOH solution B: 25 mM NaH₂PO₄/acetonitrile (3/7) buffered at pH 6.0 with 0.1N NaOHn), with a flow rate of 2 ml/min.; (internal standard: 3,5-dihydroxytoluene $t_R$ 8.84 minutes)

(f) an acidic function capable of forming salts.

(g) a salifiable basic function (h) a molecular weight of about 1891 as determined by FAB mass spectrometry.

and their pharmaceutically acceptable salts.

2. An essentially pure individual antibiotic compound selected from the group consisting of Teichomycin A₂ factor 1, Teichomycin A₂ factor 2 and Teichomycin A₂ factor 3 identified by the characteristics indicated in claim 1 and their alkali metal, alkaline earth metal or pharmaceutically acceptable ammonium salts.

3. An essentially pure individual antibiotic compound according to claim 1, consisting of Teichomycin A₂ factor 2 or its pharmaceutically acceptable salts.

4. An antibacterial composition containing from 50 to 250 mg of a compound of claim 1 as the active ingredient in combination with a pharmeceutically acceptable carrier.

* * * * *